United States Patent

Hansen et al.

[11] Patent Number: 5,614,167
[45] Date of Patent: Mar. 25, 1997

[54] TEST PATCH AND ITS USE FOR DEMONSTRATING CONTACT ALLERGY

[75] Inventors: Jens Hansen, Alleröd; Bo Kreilgård, Hilleröd, both of Denmark

[73] Assignee: Pharmacia & Upjohn AB, Stockholm, Sweden

[21] Appl. No.: 380,784

[22] Filed: Jan. 30, 1995

Related U.S. Application Data

[63] Continuation of Ser. No. 15,820, Feb. 10, 1993, abandoned, which is a continuation of Ser. No. 299,938, filed as PCT/SE88/00249, May 18, 1988, published as WO88/09184, Dec. 1, 1988, abandoned.

[30] Foreign Application Priority Data

May 25, 1987 [SE] Sweden ................... 8702190

[51] Int. Cl.$^6$ .............. A61K 49/00; A61K 31/79; A61K 9/70
[52] U.S. Cl. .............. 424/9.2; 424/78.24; 424/443; 424/445; 424/446; 424/447; 424/448; 424/449; 514/58; 514/372; 514/535; 514/642; 514/694; 514/724
[58] Field of Search ............... 424/9.2, 78.24, 424/443, 444, 445, 446, 447, 448, 449; 128/734; 514/535, 58, 724, 642, 694, 372

[56] References Cited

U.S. PATENT DOCUMENTS

| | | | |
|---|---|---|---|
| 3,699,963 | 10/1972 | Zaffaroni | 424/435 |
| 3,743,047 | 5/1973 | Zaffaroni | 180/286 |
| 4,038,485 | 7/1977 | Johnston | 435/4 |
| 4,261,973 | 4/1981 | Lee et al. | 250/559.35 |
| 4,836,217 | 6/1989 | Fischer | 128/743 |

FOREIGN PATENT DOCUMENTS

| | | |
|---|---|---|
| 0107832 | 9/1984 | European Pat. Off. |
| 0182225 | 5/1986 | European Pat. Off. |
| 252044 | 11/1987 | European Pat. Off. |
| 128846 | 8/1982 | Japan |
| 24145 | 2/1987 | Japan |

OTHER PUBLICATIONS

Chemical Abstract, vol. 107, No. 171962A (1985).
Chemical Abstract, vol. 105, No. 75409K (1981).
Chemical Abstract, vol. 98, No. 2494M (1969).

Primary Examiner—Kevin E. Weddington
Attorney, Agent, or Firm—Dinsmore & Shohl LLP

[57] ABSTRACT

$$\left[ -CH_2-CH- \atop \underset{A}{\overset{N}{\diagdown}}\underset{}{\diagup}CO \right]_n \quad (I)$$

Occlusive epicutaneous testing strip and method for demonstrating whether or not an individual suffers from contact allergy to a test substance. The test strip has at least one patch on which the test substance is incorporated in a vehicle formulated as a film which adheres to the patch and contains at least one film-forming polymer capable of absorbing moisture which when the strip is being used is secreted from the skin area tested. The characteristic feature of the strip is that on at least one of the patches on which said vehicle is formulated as a film the said polymer has the structure (I), where n is the number of times that the structure within brackets is repeated and may be ≧100, and A is a straight or branched alkylene group having a length of 3–5 carbon atoms.

7 Claims, No Drawings

TEST PATCH AND ITS USE FOR DEMONSTRATING CONTACT ALLERGY

This application is a continuation of application Ser. No. 08/015,820 filed Feb. 10, 1993, now abandoned, which is a continuation of application Ser. No. 07/299,938, filed as PCT/SE88/00249, May 18, 1988, published as WO88/09184, Dec. 1, 1988, now abandoned.

The invention is concerned with improvements of a methodology that has been developed recently for occlusive epicutaneous testing procedures and has been described in WO-A-8601994, EP-A-252,044 (=SE-A-452,251) and Br. J. Dermatol 112 (1985), pp 63–8. This method is particularly well suited for ascertaining whether or not an individual (human) suffers from a contact allergy. A test strip is applied according to this method with occlusion against the skin of the individual to be tested, said strip having at least one partial area (patch) and preferably two or more of such areas provided with test substance (contact allergen). Occlusion is achieved due to each patch being impermeable to air and moisture on the side facing away from the skin. The method of WO-A-8601994 differs in several respects from classical epicutaneous testing procedures, and among experts in this field the test strips according to WO-A-8601994 have been said to be "a new generation". The main difference, there, is that the test substance on at least one of the patches of the strip is incorporated in a vehicle that is formulated as a supple and practically entirely dry film in which the functionally most essential component is a film-forming polymer. In use, the film (the film-forming polymer) will absorb excreted substances, in the first place moisture, from the skin area to which the film has been applied. This will cause hydration of the film, and this in turn will facilitate releasing of test substance to the skin. By the method according to WO-A-8601994 it has become possible for the first time to manufacture high quality prefabricated test strips for contact allergy testing. Also it has thus become possible to lower the amount of test substance (per unit area) required and to facilitate reading of the results of the test reaction due to the fact that irritation reactions are more easily avoided.

Vaseline is the vehicle most commonly employed in classical epicutaneous testing. In some cases paper of fabric patches have been used which have been soaked in a solution of the test substance in a low molecular solvent, and in some very rare cases polymeric gels have been employed in which the test substance has been dissolved or finely dispersed, an example being triiodide ($I_3^-$ test substance) in PVP (polyvinyl pyrrolidone) dissolved in isopropanol/water (J Am Dermatol 6 (1982), pp 473–5, and Contact Dermatitis 13 (1982) pp 66–8). For a review of classical epicutaneous testing procedures see e.g. Fisher T and Maibach H I (Seminars in Dermatology 5 (1986) pp 214–24) who also discuss the WO-A-8601994 methodology in a short passage under the heading TRUE Test).

Different polymeric film layers consisting of e.g. polyvinyl pyrrolidone have been suggested as vehicles for dermal drug delivery (e.g. U.S. Pat. No. 3,699,963 and U.S. Pat. No. 3,734,097).

The present invention deals with contact allergens absorbed in certain hydrophilic polymeric films. Quite another type of allergens (causing IgE-mediated allergy) have been suggested to be absorbed and stabilized in similar polymer although without the need of film formulations (EP-A-107,832).

In our work for developing a produce according to WO-A-8601994 we have encountered difficulties in respect of certain test substances, and consequently improvements have turned out to be desirable. We have found that in many cases we have to stabilize reactive and volatile substances against degradation and physical migration from the preparations in order to be able to guarantee a standardized amount and quality of test substance to the customer. For a high-quality product it is thus not sufficient to have the strip enwrapped in packagings which are impermeable to air, moisture and light such as referred to in the contexts of earlier methods. A solution to the problem has been presented by us in EP-A-252,044 according to which unstable test substances may be formulated as an inclusion complex with a cyclo compound capable of producing such a complex with the particular test substance employed. Cyclodextrin is mentioned as a suitable cyclo compound. It has been found furthermore that the cellulose-base vehicles preferred according to WO-A-8601994 are not ideally suitable for achieving a homogenous distribution of the allergen: What happens all to easily is that drops or crystals are formed which are much too large in size and will thus result in an unsatisfactory allergen release. For us the problem has been further accentuated in the case of test substances containing a plurality of allergenic components (mix). An example is the caine mix where the optimum doses of the components are incompatible inter se in Klucel® (Hercules Inc., USA) and Metocel® (Dow Chemical Co., Midland, Mich., USA), with benzocaine being the critical component. Finally, it may be mentioned that cellulose-base vehicles when formulated as dry films together with a test substance may acquire deteriorated physico-mechanical properties with concomitant problems in handling.

The object of this invention is to provide improvements in respect of the WO-A-8601994 methodology. These are improvements that are concerned with the test strip and thus also, indirectly, are concerned with the method of carrying out the occlusive testing procedure. The invention provides a method complementary to the method described in EP-A-252,044 for stabilizing the test substance on the particular type of test strip as contemplated here. The invention provides a solution to the aforesaid problems and results in films which are more elastic and therefore easier to handle in the production procedure.

THE INVENTION

It has now been found that the aforesaid improvements can be achieved by employing as the film-forming polymer a polymer having the structure

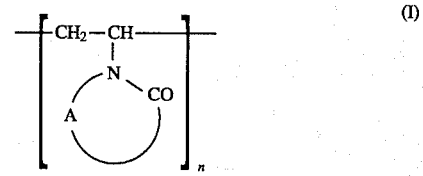

(I)

where n is the number of times that the structure within brackets is repeated and may be $\geq 100$, and A is a straight or branched alkylene bridge having a length of 3–5 carbon atoms, preferably 3 carbon atoms.

Polymers of this type are so-called N-vinylamide polymers, well-known in many technical fields. See for example Encyclopedia of Polymer Science and Technology, Plastics, Resins, Rubbers, Fibers; Vol. 14 pp 239–51; John Wiley & sons Inc. (1971). Due to their amide structures the polymers are capable of binding to low molecular compounds of various structural types. Such binding may be by way of hydrogen bonds or via dipole-dipole, dipole-ion and pi-pi interaction. The phenomenon is particularly conspicuous in the case of polyvinyl pyrrolidone (PVP, Povidone, A being propylene) and presumably caused by the then five-membered ring in conjunction with the amide structure.

In the U.S., PVP is commercially available from the GAF Corporation in the form of preparations of different mean molecular weights ($M_w$). In accordance with the present invention it is possible to employ either such individual PVP preparations or mixtures thereof, or mixtures with other polymers which are compatible with the purpose contemplated, for instance cellulose polymers. According to the invention the PVP should have a mean molecular weigth greater than or equal to 5,000 or 10,000, as e.g. greater than or equal to 25,000 daltons. Heretofore PVP has been used to a large extent in the pharmaceutical industry and is established as being physiologically tolerable, with a low degree of allergenic and irritant properties; see the aforesaid handbook, and Kneipert S et al (Die Pharmazie 28 (1973) pp 145–83).

Hydrophilic film-forming polymers having the structure (I) may be used as vehicles for a large number of test substances. For some of these, they will provide major advantages as compared to prior art technique. For other such substances the advantages will be less great although the test result obtained may be fully acceptable. Thus, if this type of polymers is employed on one, two, three, four or more patches on a strip this does not preclude the possibility of employing other hydrophilic film-forming polymers or conventional vehicles on the rest of the patches of a strip.

TEST SUBSTANCES

(Contact Allergens)

The test substances employed in the context of the present invention behave as contact allergens because when released from the test strip they are able to penetrate the skin and to give rise to a type IV allergic reaction therein. The contact allergens are as a rule of low molecular weight; usually their molecular weight is below 500 daltons even though cases have been described where the molecular weight is within the range of 500–2,000 daltons. An upper limit for a contact allergen may be set at 5,000 daltons. The contact allergens as a rule will not have a polypeptide structure.

As a matter of principle any contact allergen can be incorporated on a patch according to the invention in order to be used in an epicutaneous testing procedure for demonstrating contact allergy. Depending on the structure of the allergen and its structure-dependent physical and chemical properties various different advantages may be obtained, e.g. in respect of film handling in the manufacture of test strips, or in respect of the stability of the final preparation, or in respect of release properties, or in respect of the manner in which an irritation reaction caused by the allergen will affect readability of the sought-for allergic reaction result. In general, an allergen capable of binding to a polymer of structure (I) in the above-described way will be found to be stabilized when formulated in accordance with the invention. The manner in which this stabilization affects the final test result is of a very complex nature and can be ascertained only and solely by way of empirical results. According to results we have obtained up to now, Kathon® (Rohm and Haas, Germany) (=mixture of 5-chloro2-methyl-4-isothiazoline-3-one and the corresponding non-chloro form), mercapto mix, perfume, geraniol, cinnamic aldehyde, hydroxycitronellate, cinnamic alcohol, eugenol, isoeugenol, alpha-amyl cinnamic aldehyde, wool wax, caine mix and parabenes and cyclodextrin complexes (for example complexes of cyclodextrin plus paraform-aldehyde) when incorporated in PVP may provide advantages over the cellulose-base vehicles that are preferred according to WO-A-8601994. The advantages will vary from test substance to test substance, depending on the structure of the compounds comprised within each of these substances, and furthermore depending on the dose desired, in the exact choice of vehicle etc. In the first place, the advantages gained have resided in improved release properties. But as a main rule it may be stated that contact allergens formulated in accordance with the present invention and having polar or ionic groupings can be stabilized as compared to corresponding compounds without such groupings and therefore may potentially be administered in accordance with this invention. Examples of the groupings contemplated are primary, secondary, tertiary or quaternary amines (including their ammonium ions), carboxyl (COOH, COO$^-$, COOR with R being alkyl or aryl), ketone, aldehyde, mercapto, nitro etc. or pi-electrons as in aromatic ring systems or other conjugated double bond systems. The degree of association tendency will vary from group to group, but by way of a main rule it may be stated that said tendency is increasing in the order of nitro→ primary amine→hydroxyl→carboxyl. See for example Keipert S et al (Die Pharmazie 28 (1973) pp 145–183, especially pp 161–3) for a more detailed information as to how PVP associates with a number of different chemical compounds. It will often be the particular nature of the test substance that will decisively influence the consistency of the preparation so as to become smeary, hard, viscous or smooth. As a general rule, however, PVP may be said to be capable of forming supple films of very good physico-mechanical properties.

MANUFACTURE OF THE TEST PATCH ON WHICH THE TEST SUBSTANCE IS FORMULATED IN A FILM

There are two important steps in the manufacturing procedure which are of importance for the result obtained: The test substance has to be distributed uniformly in the film-forming material; and this latter material has to be spread out in a manner such as to form a film of uniform thickness on a suitable substrate (=film carrier). For selecting the type of film carrier to be employed see the general directions given in WO-A-8601994.

In accordance with the currently best known method for producing the film the test substance is added to the film-forming polymer (I) (vehicle) dissolved or gelled in a volatile liquid. This may be done by dispersing or emulsifying the test substance homogeneously in a finely divided state in the gel or solution. Regarding the choice of the particular polymer (I) and volatile liquid employed, it is imperative that they be such that the resultant gel when spread out is capable of forming a coherent film. Examples of volatile solvents are water, ethanol, methanol etc., or homogeneous mixtures thereof. The film carrier is then coated with uniform layer of the gel which is then allowed to dry, whereupon this material may be cut up into a suitable number of patches, these latter being preferably equal in shape and size (area). The thickness of the film as dried is variable depending on the amount of gel applied. The area of the patches may amount to 0.2–4 cm$^2$. The amount of test substance in the film per unit area thereof will vary according to the type of allergen (test substance), the exact choice of polymer (I) employed etc. Some allergens are more potent than others; the artisan will thus have to carry out some trial and error experimentation in order to find out the suitable effective amount per unit area. The term "effective amount per unit area" means the amount of test substance which when employed in the test will cause an allergic reaction in most of the sensitized or normal individuals, respectively.

The patches are then placed onto a pressure-sensitive adhesive sheet material which provides a projecting margin of at least about 1 cm all around each patch (the film side is to be placed so as to face away from the adhesive side of the material). The geometrical configuration of the patch is not critical for the purposes of the invention; so in principle strips may be employed as equivalents to other configurations.

To facilitate the testing procedure, it is possible to prearrange a plurality of patches on one common piece of the adhesive material, the individual patches having been provided with different allergens each, and/or with the same allergen in different amounts per unit area. Test strips having two or more patches are to bemused for simultaneous testing on the patient against a plurality of allergens and/or respectively, against different amounts of the same allergen per unit area. Such strips may comprise patches corresponding to a standard panel; each strip may contain up to 25, preferably up to 12 patches.

TESTING PROCEDURE

This procedure is carried out in a manner known per se but with at least one test substance formulated according to the present invention, preferably in the form of a test strip having at least one patch thereon. Thus one or more patches (test strips) of the invention are affixed on the patient so that the vehicle (film) will contact the skin in the testing area, whereupon the strip is sealingly pressed against the skin into a fixed position.

The invention is defined more precisely in the attached claims forming an integral part of the specification, and will now be illustrated by means of some non-limitative examples.

EXAMPLE 1

Manufacture of Test Strip Containing at Least One Patch Formulated in PVP Film 107.9 g of caine mix (77.1 g of benzocaine, 15.4 g of tetracaine.HCl and 15.4 g of dibucaine.HCl) were dispersed, so as to form a homogeneous mixture, in 114.3 g of polyvinyl pyrrolidone (molecular weight 1,100,000 daltons, BASF, Germany) which had been gelled in 257.1 g of water+520.6 ethanol. The mixture, which had gel consistency, was deposited and spread out as a film of even thickness (about 0.2 mm) on a polyester sheet (Mylar®, DuPont) that had a thickness of 0.075 mm and had been subjected to corona discharge treatment. After drying, a thin supple coherent film was obtained having a thickness of about 0.01 mm. In a similar manner film-coated sheets were prepared on which the test allergen was incorporated in methyl or hydroxypropyl cellulose (cp. WO-A-8601994). The film-coated sheets were then divided into 1 $cm^2$ square patches which were placed on pressure-sensitive adhesive strips (Lysapor®, Cederroth Sweden) with a projecting margin of at least 1 cm, whereupon each test strip was sealingly enclosed in aluminum foil so as to exclude light, air and moisture. The whole was then stored at +8° C. The amount of test allergen per $cm^2$ was determined initially and then again after storage as aforesaid. The method employed involved extracting a patch of known area with water and then subjecting the resultant extract to HPLC.

Similar procedures were carried out with 13.35 g of parabenes, with 11.85 g of wool wax, and with beta-cyclodextrin-paraformaldehyde inclusion complex (46.5 g beta-cyclodextrin, 3.66 g paraformaldehyde). The amount are based on 100 g of gel. The gel was prepared from approximately equal amounts of PVP, water and ethanol except in the case of the inclusion complex where ethanol was omitted and a calculated amount of about 900 g water was employed per 1,000 g of gel.

During the priority year PPD mix has been formulated similarly.

The film-coated sheets obtained from PVP gel were superior in respect of all their physico-mechanical properties.

Test strips as described above containing caine mix patches were then tested clinically on a number of patients suffering from a known type of allergy to a component of the mix. Comparative materials employed were corresponding patches formulated as set forth above in cellulose-base films or according to the Finn Chambers® method with test allergen in vaseline. Strips were placed on the patient's back under occlusion; after 48 hours they were removed, and then after still another 24 hours readings were taken. The results obtained with the patches of the invention showed good agreement with the Finn Chambers® method. The most important advantages appear for contact allergen mixtures.

We claim:

1. A method of occlusive epicutaneous testing to ascertain whether an individual suffers from contact allergy, which method comprises applying to the skin of the individual a test strip which has at least one patch having a test substance containing a plurality of allergenic components, said test substance on said at least one patch being incorporated in a vehicle which is formulated as a film adhering to the patch and containing at least one film-forming polymer (I) capable of absorbing moisture which is secreted from the skin area being tested when the strip is in use, wherein on at least one patch on which said vehicle is formulated as a film, the film forming polymer (I) is poly(N-vinyl-2-pyrrolidone), whereby a positive test result occurs when an allergic reaction is observed on the skin.

2. A method according to claim 1, wherein the test substance which is incorporated in the vehicle containing poly(N-vinyl-2-pyrrolidone) comprises allergenic components having an aromatic structure.

3. A method according to claim 1, wherein at least one of said allergenic components is selected from the group consisting of a mixture of 5-chloro-2-methyl-4-isothiazoline-3-one and 2-methyl-4-isothiazoline-3-one, mercapto mix, perfume, geraniol, cinnamic aldehyde, hydroxycitronellate, cinnamic alcohol, eugenol, isoeugenol, alpha-amyl cinnamic aldehyde, wool wax, caine mix, parabenes and cyclodextrin complexes.

4. A method according to claim 1, wherein at least one allergenic component includes a polar or ionic grouping selected from the group consisting of primary, secondary, tertiary and quaternary amines, carboxyl, ketone, aldehyde, mercapto, nitro, aromatic and non aromatic conjugated double bond groups.

5. A method of occlusive epicutaneous testing to ascertain whether an individual suffers from a contact allergy, which method comprises applying to the skin of the individual a test strip which has at least one patch having a test substance containing a plurality of allergenic components, said test substance on said at least one patch being incorporated in a vehicle which is formulated as a film adhering to the patch and containing at least one film-forming polymer (I) capable of absorbing moisture which is secreted from the skin area being tested when the strip is in use, wherein on at least one patch on which said vehicle is formulated as a film, the film-forming polymer (I) is a mixture of at least two poly(N-vinyl-2-pyrrolidone) polymers of different molecular weights, whereby a positive test result occurs when an allergic reaction is observed on the skin.

6. A method according to claim 5, wherein the test substance which is incorporated in the vehicle containing poly(N-vinyl-2-pyrrolidone) comprises allergenic components having an aromatic structure.

7. A method of occlusive epicutaneous testing to ascertain whether an individual suffers from a contact allergy, which method comprises applying to the skin of the individual a test strip which has at least one patch having a test substance containing a plurality of allergenic components, said test substance on said at least one patch being incorporated in a vehicle which is formulated as a film adhering to the patch and containing at least one film-forming polymer (I) capable of absorbing moisture which is secreted from the skin area being tested when the strip is in use, wherein on at least one patch on which said vehicle is formulated as a film, the polymer (I) has the structure

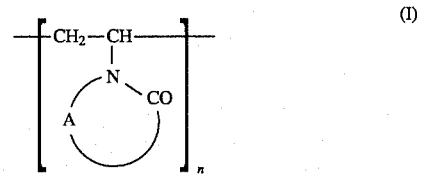

wherein n is the number of times that the structure within brackets is repeated and is $\geq 100$, and A is a straight or branched alkylene group having a length of 3–5 carbon atoms, whereby a positive test result occurs when an allergic reaction is observed on the skin.

* * * * *